United States Patent
Fingland et al.

(10) Patent No.: US 9,617,479 B2
(45) Date of Patent: Apr. 11, 2017

(54) PRODUCTION OF RENEWABLE DIESEL AND PROPYLENE

(71) Applicants: Bradley R. Fingland, Jackson, MI (US); Joseph Emmanuel Gatt, Beaumont, TX (US)

(72) Inventors: Bradley R. Fingland, Jackson, MI (US); Joseph Emmanuel Gatt, Beaumont, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 182 days.

(21) Appl. No.: 14/573,081

(22) Filed: Dec. 17, 2014

(65) Prior Publication Data

US 2015/0210932 A1    Jul. 30, 2015

Related U.S. Application Data

(60) Provisional application No. 61/933,484, filed on Jan. 30, 2014.

(51) Int. Cl.
  *C07C 1/00*  (2006.01)
  *C10G 1/00*  (2006.01)
  (Continued)

(52) U.S. Cl.
  CPC .................. *C10G 3/50* (2013.01); *C07C 7/04* (2013.01); *C10G 3/44* (2013.01); *C10G 3/47* (2013.01); *C10G 3/48* (2013.01); *C10G 3/49* (2013.01); *C10G 45/06* (2013.01); *C10G 45/10* (2013.01); *C10G 45/12* (2013.01); *C10G 69/02* (2013.01); *C10L 1/08* (2013.01); *C10L 10/14* (2013.01); *B01J 23/85* (2013.01); *C10G 2300/1014* (2013.01); *C10L 2200/0469* (2013.01); *C10L 2270/026* (2013.01); *Y02E 50/13* (2013.01); *Y02P 30/20* (2015.11)

(58) Field of Classification Search
  CPC .. C07C 1/00; C10G 1/00; C10G 73/02; C10G 53/00
  USPC ..... 585/638, 324, 327, 240, 242; 208/28, 49
  See application file for complete search history.

(56) References Cited

U.S. PATENT DOCUMENTS

2010/0163458 A1  7/2010  Daudin et al.
2010/0270207 A1  10/2010  Gomes et al.
(Continued)

FOREIGN PATENT DOCUMENTS

WO    2013148906 A1   10/2013

OTHER PUBLICATIONS

Johnson, M.F.L., "Estimation of the Zeolte of a Catalyst from Nitrogen Adsorption Isotherms", 1978, 52, pp. 425-431.
(Continued)

*Primary Examiner* — Thuan D Dang
(74) *Attorney, Agent, or Firm* — Chad A. Guice

(57) ABSTRACT

Feeds containing triglycerides are processed to produce a diesel fuel product and propylene. The diesel product and propylene are generated by deoxygenating the triglyceride-containing feed using processing conditions that enhance preservation of olefins that are present in the triglycerides. The triglyceride-containing feed is processed in the presence of a catalyst containing a Group VI metal and a Group VIII non-noble metal and in the presence of CO.

20 Claims, 2 Drawing Sheets

(51) Int. Cl.
*C10G 73/02* (2006.01)
*C10G 53/00* (2006.01)
*C10G 3/00* (2006.01)
*C10G 45/12* (2006.01)
*C10G 45/10* (2006.01)
*C10G 45/06* (2006.01)
*C10G 69/02* (2006.01)
*C10L 1/08* (2006.01)
*C10L 10/14* (2006.01)
*C07C 7/04* (2006.01)
*B01J 23/85* (2006.01)

(56) References Cited

U.S. PATENT DOCUMENTS

2011/0087058 A1* 4/2011 Harlin et al. ......... C07C 1/2078
585/240
2011/0166396 A1 7/2011 Egeberg et al.

OTHER PUBLICATIONS

PCT Application No. PCT/US2014/071156, Communication from the International Searching Authority, International Search Report and Written Opinion, Forms PCT/ISA/220, PCT/ISA/210 and PCT/ISA/237, dated Jun. 25, 2015, 10 pages.

* cited by examiner

PRODUCTION OF RENEWABLE DIESEL AND PROPYLENE

CROSS-REFERENCE TO RELATED APPLICATIONS

This application claims priority to U.S. Provisional Application Ser. No. 61/933,484 filed Jan. 30, 2014, herein incorporated by reference in its entirety.

FIELD

This invention relates to methods for processing to make diesel fuels and/or diesel additives from renewable feed sources.

BACKGROUND

Regulations related to renewable fuels provide an example of how product requirements can change over time. The United States, Canada, and the European Union have recently increased and/or are likely to increase the required amount of product from renewable sources that is contained in transportation fuels. Based on such regulatory requirements, fuels from vegetable, animal, or algae sources such as "biodiesel" will become increasingly important as a refinery product. As a result, methods are needed that will allow existing refinery equipment to produce suitable transportation fuels that incorporate increasing amounts of renewable components.

Unfortunately, the differences in chemical composition between renewable carbon sources and mineral sources pose some difficulties for refinery processing. For example, typical biologically-derived sources for fuels have oxygen contents of 1 wt % or more, possibly as much as 10 wt % or more. Conventional hydroprocessing methods can remove oxygen from a feedstock, but the by-products from deoxygenation can lead to catalyst poisoning and/or contaminant build-up in a reaction system.

One potential feedstock source for making renewable diesel products is to use a feedstock that contains triglycerides. Triglycerides are present in many typical sources used as feedstock for making renewable products. Typical triglycerides useful for making renewable products include a three carbon glycerol backbone that has ester linkages to three longer side chains. Separating the side chains from the glycerol backbone typically results in formation of a fatty acid corresponding to each of the side chains. After separation from the glycerol backbone, the fatty acids can have a chain length that is suitable for use, possibly after further processing, in diesel products such as diesel fuels or diesel fuel additives.

U.S. Patent Application Publication 2010/0163458 describes a method for converting effluents of renewable origin into fuel. The method includes the use of a supported catalyst containing $MoS_2$ and a dopant, such as phosphorus, carbon, or silicon. The method is described as favoring removal of oxygen by hydrodeoxygenation as opposed decarbonylation or decarboxylation.

U.S. Patent Application Publication 2011/0166396 describes a hydrodeoxygenation catalyst and a method for using such a catalyst. The catalyst is a supported catalyst containing Mo, with a support that includes a bimodal pore distribution. Additionally, at least 2 volume percent of the pores in the support are greater than 50 nm in diameter. The Mo catalyst with the specified pore distribution is used to perform hydrodeoxygenation on feeds containing up to 35 vol. % of renewable organic material.

U.S. Patent Application Publication 2010/0270207 describes a two stage method for processing or co-processing biomass oil containing triglycerides. The first stage includes a catalyst including only a Group VIB metal for performing hydroconversion of the triglycerides. A second stage includes a conventional hydrotreating catalyst including a Group VIB and a Group VIII metal for performing other hydroconversion reactions, such as olefin saturation and heteroatom removal.

SUMMARY OF PREFERRED EMBODIMENTS OF THE INVENTION

In one aspect, a method is provided for processing a biocomponent feedstock. The method includes exposing a feedstock, the feedstock comprising at least 40 wt % of a biocomponent feed containing triglycerides, to a first catalyst in the presence of hydrogen and at least 300 vppm of CO under first effective deoxygenation conditions for forming an at least partially deoxygenated effluent, the first catalyst comprising a Group VI metal and a Group VIII non-noble metal, the at least partially deoxygenated effluent having an oxygen content that is at least 40% less than an oxygen content of the feedstock; separating the at least partially deoxygenated effluent to form a gas phase effluent comprising propylene and a liquid phase effluent; and separating at least a portion of the propylene from the gas phase effluent.

DETAILED DESCRIPTION OF THE PREFERRED EMBODIMENTS

Figure 1:
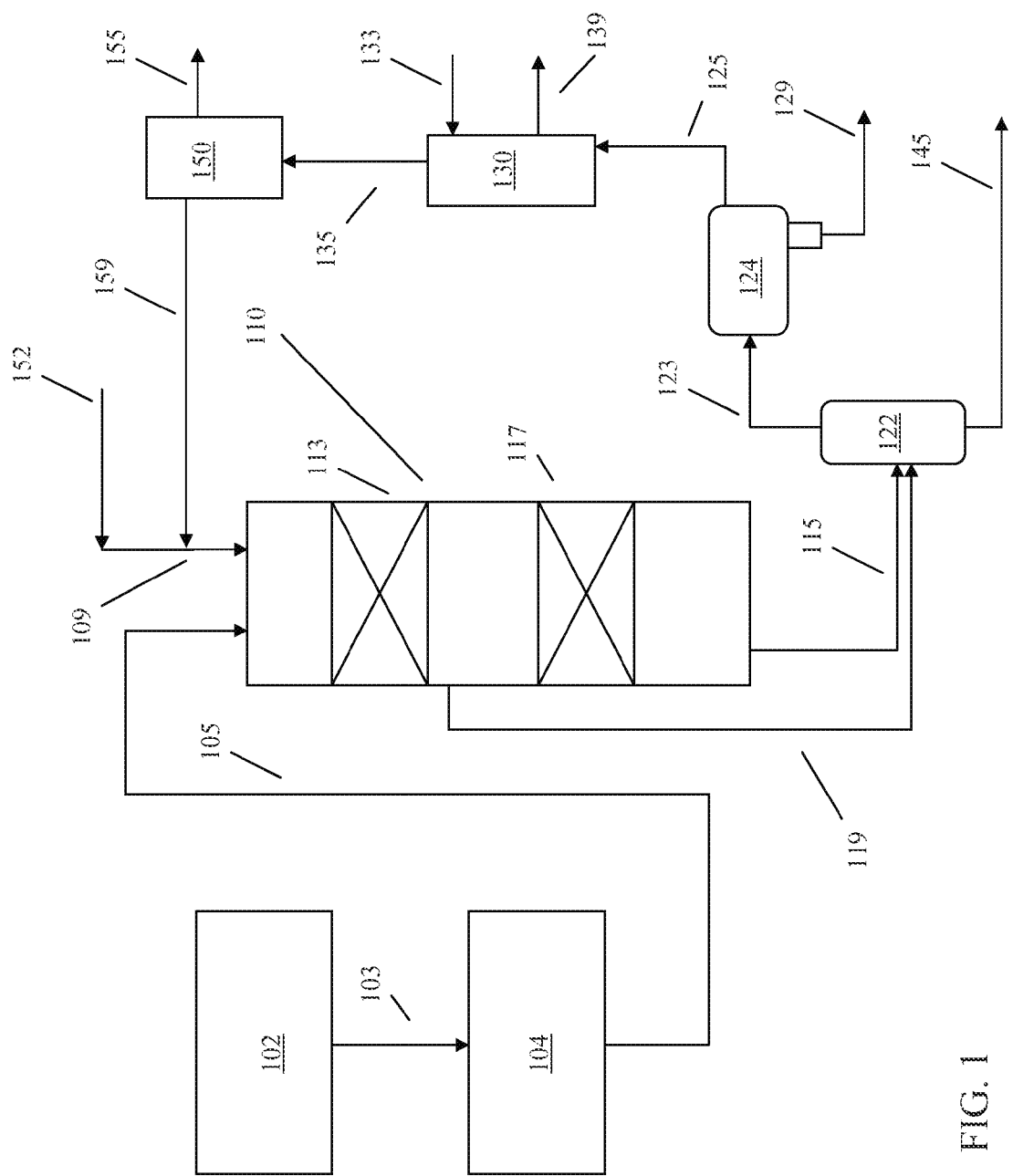
FIG. 1 schematically shows a reaction system suitable for performing a process according to an embodiment of the invention.

In various aspects, systems and methods are provided for processing a feed derived from biological sources to produce propylene as part of a process for producing a renewable diesel fuel product or additive. An example of a feed derived from a biological source is a triglyceride-containing feed. Prior to use as a diesel fuel product or additive, it is typically desirable to reduce or minimize the oxygen content of the feed. It has been unexpectedly discovered that propylene can be generated as an additional product during hydrodeoxygenation of a feed using a hydrotreating catalyst comprising both a Group VI metal and a Group VIII non-noble metal, such as a supported CoMo hydrotreating catalyst. The propylene can be generated by performing the hydrodeoxygenation in the presence of CO, which inhibits a portion of the activity of the CoMo hydrotreating catalyst for olefin saturation. The propylene is generated in place of propane, which is an expected product from separation of the side chains of a triglyceride from the backbone under hydrodeoxygenation conditions.

The above discoveries allow for additional processing options in a refinery. For example, after at least partial deoxygenation of a triglyceride-containing feed, gas phase products can be removed from the reaction system to allow for separation and recovery of propylene. Additionally, because CO is added as a component of the reaction environment in the deoxygenation stage, hydrogen used for deoxygenation of the biological feed can be recycled using conventional refinery methods. This can reduce the burden on refinery hydrogen resources, as the presence of CO in the gas phase effluent from a deoxygenation stage can create difficulties in recycling excess hydrogen for further use in the refinery.

Feedstocks

In the discussion below, a feed derived from a biological source (i.e., a biocomponent feed or feedstock) refers to a feedstock derived from a biological raw material component, such as vegetable fats/oils or animal fats/oils, fish oils, pyrolysis oils, and algae lipids/oils, as well as components of such materials, and in some embodiments can specifically include one or more types of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Examples of vegetable oils that can be used in accordance with this invention include, but are not limited to rapeseed (canola) oil, soybean oil, coconut oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, tallow oil and rice bran oil.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt % of lipids, based on total weight of the biomass itself.

Vegetable fats/oils, animal fats/oils, fish oils, pyrolysis oils, and/or algae lipds/oils as referred to herein can also include processed material. Non-limiting examples of processed vegetable, animal (including fish), and algae material include fatty acids and fatty acid alkyl esters. Alkyl esters typically include $C_1$-$C_5$ alkyl esters. One or more of methyl, ethyl, and propyl esters are preferred.

Other biocomponent feeds usable in the present invention can include any of those which comprise primarily triglycerides and free fatty acids (FFAs). The triglycerides and FFAs typically contain aliphatic hydrocarbon chains in their structure having from 8 to 36 carbons, preferably from 10 to 26 carbons, for example from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the triglyceride present in the lipid material can be comprised of $C_{10}$ to $C_{26}$ fatty acid constituents, based on total triglyceride present in the lipid material. Further, a triglyceride is a molecule having a structure corresponding to a reaction product of glycerol and three fatty acids. Although a triglyceride is described herein as having side chains corresponding to fatty acids, it should be understood that the fatty acid component does not necessarily contain a carboxylic acid hydrogen. If triglycerides are present, a majority of triglycerides present in the biocomponent feed can preferably be comprised of $C_{12}$ to $C_{18}$ fatty acid constituents, based on total triglyceride content.

Other types of feed that are derived from biological raw material components can include fatty acid esters, such as fatty acid alkyl esters (e.g., FAME and/or FAEE).

In various embodiments, the production of propylene is based on processing of triglycerides within the biocomponent feed. Thus, the presence of at least some triglycerides within the biocomponent portion of a feed is desirable. The feed can include at least about 10 wt % of feed based on a biocomponent source or sources, or at least about 25 wt %, or at least about 40 wt %, or at least about 50 wt %, or at least about 75 wt %, or at least about 90 wt %, or at least about 95 wt %. Additionally or alternately, the feed can be entirely a feed from a biocomponent source, or the feed can include about 99 wt % or less of a feed based on a biocomponent source, or about 90 wt % or less, or about 75 wt % or less, or about 50 wt % or less.

Higher amounts of feed from a biocomponent source provide an advantage based on the greater amount of renewable material, as well as potentially including a greater amount of triglycerides. Feeds with lower amounts of biocomponent materials may have other processing advantages. Such advantages can include improved flow characteristics within a reaction system, as biocomponent feeds often have a relatively high viscosity compared to conventional diesel or lubricant feeds in a refinery. Additionally, deoxygenation of a biocomponent feed generates a substantial amount of heat due to formation of highly favorable products from a free energy standpoint, such as $H_2O$ and $CO_2$. For a typical catalyst bed with a bed length of 25-30 feet (about 9-10 meters), it is preferable to have a temperature increase across the bed of 100° F. (55° C.) or less. If deoxygenation of a biocomponent feed with a high oxygen content is performed using a sufficiently reactive catalyst, an exotherm of greater than 100° F. across the catalyst bed can be generated. Blending a biocomponent feed with a portion that does not contain oxygen can reduce the exotherm generated across a catalyst bed used for performing deoxygenation.

The advantages of increased mineral feed content are largely due to dilution of the biocomponent feed, as the processing conditions effective for deoxygenation of a biocomponent feed will have a low or minimal impact on a typical hydroprocessed mineral feed. Therefore, while the dcoxygenation conditions are effective for deoxygenation of biocomponent feeds at a variety of blend ratios with mineral feeds, it is preferable to have at least about 75 wt % of the feed from a biocomponent source, such as at least about 90 wt %/o or at least about 95 wt %.

One option for increasing the biocomponent content of a feed while retaining some of the benefits of adding a feed with reduced oxygen content is to use recycled product from processing of biocomponent feed as a diluent. A recycled product from processing a biocomponent feed is still derived from a biocomponent source, and therefore such a recycled product is counted as a feed portion from a biocomponent source. Thus, a feed containing 60% biocomponent feed that has not been processed and 40% of a recycled product from processing of the biocomponent feed would be considered as a feed that includes 100% of feed from a biocomponent source. As an example, at least a portion of the product from processing of a biocomponent feed can be a diesel boiling range product. Such a recycled diesel boiling range product will be deoxygenated, and therefore incorporation of the recycled diesel boiling range product in the feed will reduce the exotherm generated during deoxygenation. Adding a recycled diesel boiling range product is also likely to improve the cold flow properties of a biocomponent feed.

More generally, any convenient product from processing of a biocomponent feed can be recycled for blending with the biocomponent feed in order to improve the cold flow properties and/or reduce the oxygen content of the input flow to a deoxygenation process. If a recycled product flow is added to the input to a deoxygenation process, the amount of recycled product can correspond to at least about 10 wt % of the feed to the deoxygenation process, such as at least about 25 wt %, or at least about 40 wt %. Additionally or alternatively, the amount of recycled product in a feed can be about 60 wt % or less, such as about 50 wt % or less, 40 wt % or less, or about 25 wt % or less.

While feed dilution can be used to control the exotherm generated across a catalyst bed used for deoxygenation, it is noted that some processing options can also impact the exotherm. One alternative is to use a less reactive catalyst, so that a larger amount of catalyst is needed at a given liquid hourly space velocity (LHSV) in order to deoxygenate a feed to a desired level. Another option is to reduce the amount of hydrogen provided for the deoxygenation process. Still another option could be to introduce additional features into a reactor to assist in cooling and/or transporting heat away from a deoxygenation catalyst bed. In combination with selecting an appropriate amount of product recycle and/or blending of another non-oxygenated feed, a desired combination of a flow characteristics and heat generation during deoxygenation can be achieved.

With regard to triglyceride content, the feedstock can include at least about 1 wt % of triglycerides, such as at least about 15 wt %, or at least about 25 wt %, or at least about 40 wt %, or at least about 50 wt %, or at least about 75 wt %, or at least about 90 wt %. Additionally or alternatively, the feed can be composed entirely of triglycerides, or the triglyceride content of the feed can be about 95 wt % or less, such as about 90 wt % or less, or about 75 wt % or less, or about 50 wt % or less, or about 40 wt % or less, or about 25 wt % or less. If propylene production is also desirable, feeds with higher triglyceride contents are preferred, such as feeds including at least about 15 wt % of triglycerides, or at least about 25 wt % triglycerides, or at least about 40 wt %, or at least about 50 wt %, or at least about 75 wt %, or at least about 90 wt %. Alternatively, under some conditions propylene production may be enhanced by processing a feed containing a suitable range of triglycerides, such as a feed containing from about 15 wt % to about 40 wt % triglycerides, preferably about 25 wt % to about 35 wt %.

The biocomponent portion of a feedstock can also be characterized relative to the olefin content of the feed. The olefin content of a biocomponent feed can vary widely depending on the source of the feed. For example, a feed based on soybean oil may contain up to 100% of molecules that contain at least one degree of unsaturation. Palm oils typically include 25-50 wt % of olefinic molecules, while coconut oil may include 15% or less of olefinic molecules. Depending on the embodiment, a biocomponent portion of a feed can include at least about 20 wt % olefins, such as at least about 40 wt % olefins, or at least about 50 wt % olefins, or at least about 75 wt % olefins. As defined herein, an olefin refers to any compound that includes an olefin bond. Thus, there are two ways that the wt % of olefins in a feed can be modified. If all olefins in a molecule are saturated, the molecule is no longer an olefin. Alternatively, if a molecule is broken down into smaller components, such as by deoxygenation or cracking, the wt % of olefins may be reduced if one or more of the smaller components does not contain an olefin. As an example, a triglyceride with an olefin bond in only one of the three side chains would be considered an olefin as defined herein. Therefore, the entire weight of the triglyceride would count toward the olefin weight percentage in the feed. After a deoxygenation that preserved olefin bonds, only the fatty acid resulting from the side chain including the olefin bond would count toward the olefin weight percentage. The other two fatty acids formed from the side chains would be separate molecules and therefore would not be considered olefins. Thus, even though no olefins were saturated, the weight percentage of olefins in the feed would still be lower.

In an embodiment, the biocomponent portion of the feedstock (such as the triglycerides) can be a non-hydrotreated portion. A non-hydrotreated feed can typically have an olefin content and an oxygen content similar to the content of the corresponding raw biocomponent material. Examples of suitable biocomponent feeds can include food grade vegetable oils, and biocomponent feeds that are refined, bleached, and/or deodorized.

Biocomponent based diesel boiling range feedstreams can have a wide range of nitrogen and/or sulfur contents. For example, a biocomponent based feedstream based on a vegetable oil source can contain up to about 300 wppm nitrogen. In contrast, a biomass based feedstream containing whole or ruptured algae can sometimes include a higher nitrogen content. Depending on the type of algae, the nitrogen content of an algae based feedstream can be at least about 2 wt %, for example at least about 3 wt %, at least about 5 wt %, or at least about 10 wt %, and algae with still higher nitrogen contents are known. The sulfur content of a biocomponent feed can also vary. In some embodiments, the sulfur content can be about 500 wppm or less, for example about 100 wppm or less, about 50 wppm or less, or about 10 wppm or less.

Aside from nitrogen and sulfur, oxygen can be another heteroatom component in biocomponent based feeds. A biocomponent diesel boiling range feedstream based on a vegetable oil, prior to hydrotreatment, can include up to about 10 wt % oxygen, for example up to about 12 wt % or up to about 14 wt %. Additionally or alternatively, such a biocomponent diesel boiling range feedstream can include at least about 1 wt % oxygen, for example at least about 2 wt %, at least about 3 wt %, at least about 4 wt %, at least about 5 wt %, at least about 6 wt %, or at least about 8 wt %. Further additionally or alternatively, a biocomponent feedstream, prior to hydrotreatment, can include an olefin content of at least about 3 wt %, for example at least about 5 wt % or at least about 10 wt %.

A mineral feedstock refers to a conventional (e.g., non-biocomponent) feedstock, typically derived from crude oil and that has optionally been subjected to one or more separation and/or other refining processes. In one preferred embodiment, the mineral feedstock can be a petroleum feedstock boiling in the diesel range or above. Examples of suitable feedstocks can include, but are not limited to, virgin distillates, hydrotreated virgin distillates, kerosene, diesel boiling range feeds (such as hydrotreated diesel boiling range feeds), light cycle oils, atmospheric gasoils, and the like, and combinations thereof.

Mineral feedstocks for blending with a biocomponent feedstock can be relatively free of nitrogen (such as a previously hydrotreated feedstock) or can have a nitrogen content from about 1 wppm to about 2000 wppm nitrogen, for example from about 50 wppm to about 1500 wppm or from about 75 to about 1000 wppm. In some embodiments, the mineral feedstock can have a sulfur content from about 1 wppm to about 10,000 wppm sulfur, for example from about 10 wppm to about 5,000 wppm or from about 100 wppm to about 2,500 wppm.

Preferably, a mineral feedstock for blending with a biocomponent feedstock can be a mineral feedstock with a relatively low sulfur content, such as a hydrotreated mineral feedstock. The single metal catalysts described below have relatively low activity for performing desulfurization and for hydrogenating or saturating olefins. This allows olefins to be (at least partially) preserved in the propylene product and diesel boiling range molecules generated after exposure to the single metal catalysts. In order to preserve these olefins, it may be desirable to avoid subsequent hydrotreatment of a biocomponent feedstock using a conventional hydrotreating catalyst with conventional hydotreating conditions. Using a mineral feedstock for blending that contains a sufficiently low sulfur content can allow a resulting product to meet a desired sulfur specification without requiring a subsequent hydrotreatment under conditions that saturate olefins. As an alternative, if additional saturation of olefins in diesel boiling range molecules is desired, the olefins in propylene can be preserved by separating out propylene prior to any subsequent hydrotreatment. Such preferred feedstocks can be relatively free of sulfur, or can have a sulfur content from about 1 wppm to about 500 wppm, such as from about 10 wppm to about 200 wppm of sulfur or from about 20 wppm to about 100 wppm of sulfur. Additionally or alternately, the combined (biocomponent plus mineral) feedstock can have a sulfur content of at least about 5 wppm, for example at least about 10 wppm, at least about 25 wppm, or at least about 100 wppm. Further additionally or alternately, the combined feedstock can have a sulfur content of about 500 wppm or less, about 100 wppm or less, or about 50 wppm or less. Still further additionally or alternately, the nitrogen content of the combined feedstock can be about 1000 wppm or less, for example about 500 wppm or less, about 100 wppm or less, about 50 wppm or less, about 30 wppm or less, about 20 wppm or less, or about 10 wppm or less.

The content of sulfur, nitrogen, oxygen, and olefins in a feedstock created by blending two or more feedstocks can typically be determined using a weighted average based on the blended feeds. For example, a mineral feed and a biocomponent feed can be blended in a ratio of 80 wt % mineral feed and 20 wt % biocomponent feed. If the mineral feed has a sulfur content of about 1000 wppm, and the biocomponent feed has a sulfur content of about 10 wppm, the resulting blended feed could be expected to have a sulfur content of about 802 wppm.

The boiling range for biocomponent feedstreams suitable for use according to the invention can vary depending on the nature of the biocomponent source. Biocomponent feedstreams with final boiling points up to about 1000° F. (538° C.) may be suitable for use, as the triglycerides within a biocomponent feedstream will have a higher boiling point than the boiling point of the individual chains attached to the glycerol backbone. Mineral feedstreams suitable for use as a blending component tend to boil within the range of about 215° F. (about 102° C.) to about 800° F. (about 427° C.). Preferably, a mineral feedstream has an initial boiling point of at least about 215° F. (about 102° C.), for example at least about 250° F. (about 121° C.), at least about 275° F. (about 135° C.), at least about 300° F. (about 149° C.), at least about 325° F. (about 163° C.), at least about 350° F. (about 177° C.), at least about 400° F. (about 204° C.), or at least about 451° F. (about 233° C.). Preferably, a mineral feedstream has a final boiling point of about 800° F. (about 427° C.) or less, or about 750° F. (about 399° C.) or less. Additionally or alternately, a feedstock can be characterized by the boiling point required to boil a specified percentage of the feed. For example, the temperature required to boil at least 5 wt % of a feed is referred to as a "T5" boiling point. A suitable mineral (petroleum) feedstock can have a T5 boiling point of at least about 230° F. (about 110° C.), for example at least about 250° F. (about 121° C.) or at least about 275° F. (about 135° C.). Further additionally or alternately, the mineral (petroleum) feedstock can have a T95 boiling point of about 775° F. (about 418° C.) or less, for example about 750° F. (about 399° C.) or less or about 725° F. (about 385° C.) or less. In another embodiment, the diesel boiling range feedstream can also include kerosene range compounds to provide a feedstream with a boiling range from about 250° F. (about 121° C.) to about 800° F. (about 427° C.).

Reactions for Oxygen Removal

Oxygen removal during hydroprocessing of a feedstock typically occurs via one of three reaction pathways. One potential reaction pathway is hydrodeoxygenation. In a hydrodeoxygenation reaction, oxygen is removed from feed molecule as water. The carbon chain for the feed molecule remains intact after a typical hydrodeoxygenation reaction. Water is a contaminant that can potentially contribute to deactivation of some hydrotreating catalysts, such as NiMo or CoMo type catalysts. However, by itself water does not lead to corrosion within a reaction system. Additionally, removing oxygen as water maintains the chain length of a feed molecule. Maintaining the chain length of molecules intended for use as a fuel or fuel blending product is usually beneficial, as it means that a greater percentage of the carbon from the feed is incorporated into the final fuel product.

Hydrodecarboxylation removes oxygen by forming $CO_2$ from biofeeds. This $CO_2$ forms carbonic acid when combined with water. Carbonic acid corrosion may require metallurgical upgrades to carbon steel in downstream equipment, particularly fin fans, heat exchangers, and other locations that liquid water will be present prior to a an amine scrubbing system or other system for removing $CO_2$.

Hydrodecarbonylation removes oxygen by forming CO from biofeeds. CO is a known inhibitor for hydrodesulfurization. For example, 1000 ppm CO can deactivate a conventional CoMo catalyst by 10%. CO is also not removed in appreciable quantities by conventional amine scrubbing systems. As such, CO can build up through gas recycle and can be cascaded to downstream hydrotreatment, dewaxing, and/or hydrofinishing stages. As a result, removing oxygen from a biocomponent feed as CO may require the use of pressure swing adsorbers (including rapid cycle pressure swing adsorbers) or other gas cleaning equipment in order to remove CO from a reaction system.

Depending on the conditions present in a reactor, the relative amounts of CO and $CO_2$ in a reactor can be modified by the water gas shift reaction. Additionally or alternately, a separate water gas shift stage can be used to modify the CO content of an effluent withdrawn from a reactor. The water gas shift reaction is an equilibrium reaction that can convert $CO_2$ and $H_2$ into CO and $H_2O$. Due to the water gas shift reaction, the amount of decarbonylation and decarboxylation may not be clear, due to conversion from one form of carbon oxide to another. Hydrodeoxygenation can be distinguished at least in part from decarbonylation and decarboxylation by characterizing the odd versus even numbered carbons in a deoxygenated product.

Most catalysts used for performing a catalytic deoxygenation of a bicomponent feed will be less than 100% selective for a given pathway. Instead, at least some deoxygenation of a feed will occur via each of the three pathways mentioned above during a typical catalytic deoxygenation of a feed. The relative amounts of deoxygenation by each method will vary depending on the nature of the catalyst and the reaction conditions.

Because feeds derived from biological sources typically have carbon chains with even numbers of carbon molecules, hydrodeoxygenation can be distinguished from decarbonylation and decarboxylation based on the carbon chain length of the resulting molecules. Hydrodeoxygenation typically leads to production of molecules with an even number of carbon atoms while decarbonylation and decarboxylation lead to molecules with an odd number of carbon atoms.

Hydroprocessing Conditions—Deoxygenation

One option for deoxygenating a feed derived from a biological source is to expose the feed to a hydrotreating catalyst under effective hydrodeoxygenation conditions. Although hydrotreating catalysts are suitable for deoxygenation of feedstocks, the activity of most hydrotreating catalysts is sufficiently high that olefin saturation is also performed under the conventional deoxygenation conditions. Such olefin saturation would result information of propane during deoxygenation of triglycerides. To allow for formation of propylene, CO can be introduced as part of the hydrogen treat gas used for the effective hydrodeoxygenation conditions.

The CO can be present in the treat gas, for example, based on recycling a portion of the gas phase effluent from the hydrodeoxygenation reaction. Although many methods are available for removal of $CO_2$ from a gas phase effluent, such as using an amine scrubber, such methods are less effective for removal of CO. After cleaning up the gas phase effluent from the hydrodeoxygenation reaction, a majority of the CO present in the gas phase effluent can remain in the cleaned effluent. Recycling a portion of this gas phase effluent to the hydrodeoxygenation reactor can allow for a buildup of CO in the reactor to a desired level for reducing the olefin saturation activity of the hydrotreating catalyst(s) in the reactor. The amount of CO in the recycled portion of the treat gas can be controlled by adjusting the amount of gas phase effluent that is returned to the reactor as a recycled gas. This can be achieved by, for example, only recycling a portion of the effluent, or by having a bleed stream that is removed from the recycled effluent (or recycled portion of the effluent), or by any other convenient method. Additionally or alternately, a separate CO source can be used to provide a desired amount of CO for the hydrogen treat gas, if the amount of CO in the recycled effluent (or recycled portion of the effluent) is insufficient.

In various aspects, the amount of CO present in the reaction environment can be at least about 300 vppm, such as at least about 500 vppm, or at least about 750 vppm, or at least about 1000 vppm, or at least about 1500 vppm. Additionally or alternately, the amount of CO present in the reaction environment can be at about 7000 vppm or less, such as about 5000 vppm or less, or about 4000 vppm or less, or about 3000 vppm or less, or about 2000 vppm or less. At equilibrium, the amount of CO in the total treat gas introduced into the reactor can be similar to the amount of CO present in the reaction environment in the reactor. It is noted that the amount of CO present in the reaction environment may be lower at the beginning of operation for a reactor. In aspects where at least a portion of the CO is provided based on deoxygenation of feedstock, some initial processing time may be required to reach the equilibrium level of CO based on the feed being processed, the amount of effluent being recycled, and/or the amount of recycled effluent that is removed as a bleed or side stream prior to introduction into the reactor.

A catalyst suitable for oxygen removal during processing of a biocomponent portion of a feedstock can be a supported metal sulfide catalyst. The metal can be one or more Group VI metals (corresponding to Group 6 of the modern IUPAC periodic table) such as Mo or W, or one or more Group VIII non-noble metals (corresponding to Groups 8-10 of the modern IUPAC periodic table) such as Ni or Co. The support for the catalyst can be any convenient type of support, such as alumina, silica, zirconia, titania, amorphous carbon, or combinations thereof. One example of a suitable catalyst is a supported CoMo hydrotreating catalyst.

The catalysts used for hydrodeoxygenation can include conventional hydroprocessing catalysts, such as those that comprise at least one Group VIII non-noble metal (Columns 8-10 of IUPAC periodic table), preferably Fe, Co, and/or Ni, such as Co and/or Ni; and at least one Group VI metal (Column 6 of IUPAC periodic table), preferably Mo and/or W. Such hydroprocessing catalysts can optionally include transition metal sulfides. These metals or mixtures of metals are typically present as oxides or sulfides on refractory metal oxide supports. Suitable metal oxide supports include low acidic oxides such as silica, alumina, titania, zirconia, amorphous carbon, silica-titania, titania-alumina, and combinations thereof. Suitable aluminas are porous aluminas such as gamma or eta having average pore sizes from 50 to 200 Å, or 75 to 150 Å; a surface area from 100 to 300 $m^2/g$, or 150 to 250 $m^2/g$; and a pore volume of from 0.25 to 1.0 $cm^3/g$, or 0.35 to 0.8 $cm^3/g$. The supports are preferably not promoted with a halogen such as fluorine as this generally increases the acidity of the support.

The at least one Group VIII non-noble metal, in oxide form, can typically be present in an amount ranging from about 2 wt % to about 40 wt %, preferably from about 4 wt % to about 15 wt %. The at least one Group VI metal, in oxide form, can typically be present in an amount ranging from about 2 wt % to about 70 wt %, preferably for supported catalysts from about 6 wt % to about 40 wt % or from about 10 wt % to about 30 wt %. These weight percents are based on the total weight of the catalyst. Suitable metal catalysts include cobalt/molybdenum (1-10% Co as oxide, 10-40% Mo as oxide), nickel/molybdenum (1-10% Ni as oxide, 10-40% Co as oxide), or nickel/tungsten (1-10% Ni as oxide, 10-40% W as oxide) on alumina, silica, silica-alumina, zirconia, titania, or a combination thereof.

Alternatively, the hydrotreating catalyst can be a bulk metal catalyst, or a combination of stacked beds of supported and bulk metal catalyst. By bulk metal, it is meant that the catalysts are unsupported wherein the bulk catalyst particles comprise 30-100 wt. % of at least one Group VIII non-noble metal and at least one Group VIB metal, based on the total weight of the bulk catalyst particles, calculated as metal oxides and wherein the bulk catalyst particles have a surface area of at least 10 $m^2/g$. It is furthermore preferred that the bulk metal hydrotreating catalysts used herein comprise about 50 to about 100 wt %, and even more preferably about 70 to about 100 wt %, of at least one Group VIII non-noble metal and at least one Group VIB metal, based on the total weight of the particles, calculated as metal oxides. The amount of Group VIB and Group VIII non-noble metals can easily be determined VIB TEM-EDX.

Bulk catalyst compositions comprising one Group VIII non-noble metal and two Group VIB metals are preferred. It has been found that in this case, the bulk catalyst particles are sintering-resistant. Thus the active surface area of the bulk catalyst particles is maintained during use. The molar ratio of Group VIB to Group VIII non-noble metals ranges generally from 10:1-1:10 and preferably from 3:1-1:3. In the case of a core-shell structured particle, these ratios of course apply to the metals contained in the shell. If more than one Group VIB metal is contained in the bulk catalyst particles, the ratio of the different Group VIB metals is generally not critical. The same holds when more than one Group VIII non-noble metal is applied. In the case where molybdenum and tungsten are present as Group VIB metals, the molybdenum:tungsten ratio preferably lies in the range of 9:1-1:9. Preferably the Group VIII non-noble metal comprises nickel and/or cobalt. It is further preferred that the Group VIB metal comprises a combination of molybdenum and tungsten. Preferably, combinations of nickel/molybdenum/tungsten and cobalt/molybdenum/tungsten and nickel/cobalt/molybdenum/tungsten are used. These types of precipitates appear to be sinter-resistant. Thus, the active surface area of the precipitate is maintained during use. The metals are preferably present as oxidic compounds of the corresponding metals, or if the catalyst composition has been sulfided, sulfidic compounds of the corresponding metals.

It is also preferred that the bulk metal hydrotreating catalysts used herein have a surface area of at least 50 m$^2$/g and more preferably of at least 100 m$^2$ g. It is also desired that the pore size distribution of the bulk metal hydrotreating catalysts be approximately the same as the one of conventional hydrotreating catalysts. Bulk metal hydrotreating catalysts have a pore volume of 0.05-5 ml/g, or of 0.1-4 ml/g, or of 0.1-3 ml/g, or of 0.1-2 ml/g determined by nitrogen adsorption. Preferably, pores smaller than 1 nm are not present. The bulk metal hydrotreating catalysts can have a median diameter of at least 50 nm, or at least 100 nm. The bulk metal hydrotreating catalysts can have a median diameter of not more than 5000 μm, or not more than 3000 pun. In an embodiment, the median particle diameter lies in the range of 0.1-50 μm and most preferably in the range of 0.5-50 μm.

The hydroprocessing catalyst can be provided in a reactor in one or more catalyst beds. For example, a convenient bed length in some reactors is a bed length of about 25 feet to 30 feet. Such a bed length reduces difficulties in a catalyst bed associated with poor flow patterns. Due to the reduced reactivity from introduction of CO into the reaction environment, and due to potential concerns from excessive heat generation from having a catalyst bed with larger amounts of catalyst, multiple beds may be preferable for achieving a desired level of deoxygenation.

Typical effective conditions for processing a feedstock containing triglycerides to remove oxygen can include conditions effective for hydrodeoxygenation, decarbonylation, and/or decarboxylation. A variety of conditions may be suitable as effective conditions. The pressure during processing of a feedstock for oxygen removal can correspond to a hydrogen partial pressure of about 200 psig (1.4 MPag) to about 700 psig (4.8 MPag). For example, the hydrogen partial pressure can be at least about 200 psig (1.4 MPag), or at least about 250 psig (1.7 MPag), or at least about 300 psig (2.1 MPag), or at least about 400 psig (2.8 MPag). Additionally or alternately, the hydrogen partial pressure can be about 700 psig (4.8 MPag) or less, such as about 600 psig (4.1 MPag) or less, or about 500 psig (3.4 MPag) or less, or about 450 psig or less (3.1 MPag). It is noted that for aspects where the hydroprocessing catalyst includes Ni, hydrogen partial pressures of about 500 psig (3.4 MPag) or less are preferred in order to avoid potential production of nickel carbonyl species. Lower hydrogen partial pressures are also beneficial for reducing or minimizing the amount of olefin saturation, including the amount of saturation from propylene to propane that occurs during deoxygenation.

The effective conditions for oxygen removal can also include a temperature, a hydrogen treat gas rate, and a liquid hourly space velocity (LHSV). Suitable effective temperatures can be from about 230° C. to about 375° C., such as at least about 250° C. or less than about 350° C. The LHSV can be from about 0.1 hr$^{-1}$ to about 10 hr$^{-1}$, such as from about 0.2 hr$^{-1}$ to about 5.0 hr$^{-1}$. The hydrogen treat gas rate can be any convenient value that provides sufficient hydrogen for deoxygenation of a feedstock. Typical values can range from about 500 scf/B (84 Nm$^3$/m$^3$) to about 10,000 scf/B (1685 Nm$^3$/m$^3$). One option for selecting a treat gas rate can be to select a rate based on the expected stoichiometric amount of hydrogen for complete deoxygenation of the feedstock. For example, many types of biocomponent feeds have a stoichiometric hydrogen need for deoxygenation of between 200 scf/B (34 Nm$^3$/m$^3$) to about 1500 scf/B (253 Nm$^3$/m$^3$), depending on the mechanism for oxygen removal. In some aspects, the hydrogen treat gas rate can be selected based on a multiple of the stoichiometric hydrogen need, such as at least about 1 times the hydrogen need, or at least about 1.5 times the hydrogen need, or at least about 2 times the hydrogen need. In other aspects where at least a portion of the gas phase deoxygenation effluent is recycled, any convenient amount of hydrogen relative to the stoichiometric need can be used.

With regard to the hydrogen-containing treat gas, the hydrogen-containing treat gas can be composed of a recycled portion and a make-up portion. The make-up portion of hydrogen-containing treat gas can correspond to a fresh source of hydrogen-containing gas, a hydrogen-containing gas stream from a recycle loop not associated with the deoxygenation reaction system, or another convenient source. The recycled portion of the hydrogen-containing treat gas can be formed based on the effluent from the reaction system and/or the effluent withdrawn at an intermediate location between reaction stages. For example, a gas phase portion of the effluent from the deoxygenation reaction system can be separated from a liquid phase portion by any convenient method. Various light ends, such as propylene, can be separated from the gas phase effluent. The separation of propylene and/or other light ends can preferably occur prior to $CO_2$, but the separation can also be performed after $CO_2$ removal. For $CO_2$ removal, the gas phase effluent can be treated in any convenient manner, such as passing the gas phase effluent through an amine scrubber system. Such a system may also be suitable for removal of $H_2S$. If desired, water can be removed from the gas phase effluent before, during, or after $CO_2$ removal. The result of the various separation steps can be a hydrogen-containing stream that also contains CO. In order to allow the CO concentration in the reactor to reach a steady state, a bleed or side stream can be removed from the gas phase effluent at any convenient location (either before or after any of the above separation steps). Due to the difficulty in removing CO without resorting to a membrane separation and/or a pressure swing adsorption type apparatus, use of a bleed stream provides a method for removing a portion of the CO in the gas phase effluent. After the above separation steps and the removal of the bleed stream, a make-up stream of a hydrogen-containing gas can be added to the gas phase effluent to achieve the desired volume flow of gas for input to the reaction system.

An additional consideration during deoxygenation is maintaining the sulfided state of the catalyst. If little or no sulfur is present in the reaction environment, the sulfided metal on the catalyst will have a tendency to be reduced and/or converted to oxide form, leading to reduced deoxygenation activity for the catalyst. To maintain catalyst activity, some sulfur can be introduced into the reaction environment. The sulfur can be introduced as sulfur in a mineral feed that is blended with the triglyceride-containing biocomponent feed. Additionally or alternately, sulfur can be introduced as part of the gas phase environment, such as by using an $H_2$ source that contains some $H_2S$. The amount of sulfur present in the reaction environment can be at least about 100 wppm, such as at least about 200 wppm or at least about 500 wppm. If this sulfur is introduced as a gas phase component (such as $H_2S$), the sulfur can be easily removed from any liquid products using a gas-liquid separation. If the sulfur is introduced as part of the feed, it may be feasible to blend the resulting products to achieve an acceptable sulfur level in any final product. Alternatively, subsequent hydroprocessing can be used to reduce the sulfur level of the products, if olefin preservation is not desired.

The effective conditions for deoxygenation can be suitable for reducing the oxygen content of the feed to less than about 1.0 wt %, such as less than about 0.5 wt % or less than about 0.2 wt %. Although the stoichiometric hydrogen need is calculated based on complete deoxygenation, reducing the oxygen content to substantially zero is typically not required to allow further processing of the deoxygenated feed in conventional equipment. Alternatively, in some aspects the effective conditions can be selected to perform at least a partial deoxygenation of the feedstock. A partial deoxygenation corresponds to conditions suitable for reducing the oxygen content of the feed by at least about 40%, such as by at least about 50% or at least about 75%. Without being bound by any particular theory, it is believed that separation of the side chains of a triglyceride from the three carbon backbone occurs relatively early during deoxygenation of a feed. As a result, when propylene production is desired, partial deoxygenation of a triglyceride-containing feed can be beneficial for generating propylene while reducing or mitigating olefin saturation.

In some aspects, the deoxygenation reaction can be performed in multiple stages, with intermediate separation occurring between stages to allow for removal of gas phase effluent. Such intermediate separation can allow for recovery of propylene at one or more intermediate locations in a reaction system, so that propylene formed in an earlier reaction stage can be removed before it is potentially saturated in a later stage. In such aspects, the deoxygenation conditions can be selected so that each stage performs a part of the deoxygenation in order to achieve a desired final amount of deoxygenation. In aspects with multiple stages, each stage can perform about 20% to about 80% deoxygenation relative to the amount of oxygen in the initial feed. For example, a reaction stage can perform at least about 25% deoxygenation (relative to the amount of oxygen in the initial feed prior to entering the deoxygenation stages), or at least about 33%, or at least about 45%. Additionally or alternately, a stage can perform about 75% deoxygenation or less, or about 60% deoxygenation or less, or about 50% deoxygenation or less, or about 40% deoxygenation or less.

Properties of Deoxygenated Product

Triglycerides derived from biological sources typically include one or more olefins in some or all of the fatty acid chains attached to the glycerol backbone. For naturally occurring triglycerides, a variety of fatty acid chains will be present, with variations between the fatty acid chains present even within a single triglyceride. The fatty acid chains in a triglyceride from a biological source commonly have between 1 to 2 olefins per fatty acid chain, such as an average of about 1.5. During deoxygenation of a biocomponent feed under conventional hydrotreating conditions, such olefins are readily saturated, resulting in loss of 75% or more of the olefins originally present in the fatty acid chains. By contrast, deoxygenation of a biocomponent feed under the effective deoxygenation conditions described herein can allow for deoxygenation of the feed while preserving an increased amount of olefins present in the fatty acid chains. Typically, olefins occurring naturally in a fatty acid chain that is part of a triglyceride will be internal olefins, as opposed to alpha olefins.

The amount of olefins present in a diesel boiling range product produced by deoxygenation of a triglyceride-containing feed can vary depending on a variety of factors. These factors include the number of olefins present in the feed, the type of catalyst, and the deoxygenation conditions. Since the olefins present after deoxygenation represent olefins that were preserved during deoxygenation, the olefins will typically be internal olefins. This is in contrast to alpha olefins, which sometimes can be created under sufficiently severe conditions in the presence of catalysts that include a Group VIII metal. The number of olefins present in the diesel boiling range product can correspond to at least 20% of the olefins present in the side chains of the triglycerides in the feed, such as at least 25% or at least 30%. Relative to the number of diesel boiling range molecules, the number of diesel boiling range molecules containing an olefin can be at least about 10% of the molecules, such as at least about 15%, and preferably at least about 20% or at least about 25%.

Another method for characterizing the olefin content of a feed or product is in terms of the number of olefin bonds (carbon-carbon double bonds) relative to the number of "paraffin bonds" (carbon-carbon single bonds). For example, an alkane containing 17 carbon atoms will have 16 carbon-carbon single bonds. A corresponding 17 carbon atom molecule with one olefin bond will have 15 carbon-carbon single bonds and 1 carbon-carbon double bond. Such an alkene would have a ratio of olefin bonds to paraffin bonds of 1/15=0.067. This type of ratio is defined herein as an olefin to paraffin ratio.

The fatty acid side chains of a typical triglyceride molecule have an average of about 1.5 olefins per side chain. For a 12 carbon side chain, this corresponds to an olefin to paraffin ratio of 1.5/9.5 or 0.158. For an 18 carbon side chain, this corresponds to an olefin to paraffin ratio of 1.5/15.5 or 0.097. One indicator of the amount of olefin saturation is the olefin to paraffin ratio for the resulting diesel or distillate product after deoxygenation. Depending on the embodiment, the olefin to paraffin ratio for a deoxygenated product can be at least about 0.02, such as at least about 0.03 and preferably at least about 0.04 or at least about 0.05.

A diesel fuel or diesel fuel additive that includes olefinic molecules will have different properties than a similar diesel fuel or diesel fuel additive containing only paraffinic molecules. The presence of one or more olefins typically lowers the cetane rating of a molecule relative to a paraffinic molecule having the same number of carbon atoms. The presence of one or more olefins also typically improves the cold flow properties of a molecule, such as by reducing the cloud point or pour point relative to a paraffinic molecule having the same number of carbons.

This exchange of a lower cetane rating for improved cold flow properties can be beneficial for a diesel fuel or fuel additive based on a biocomponent feed. Due to the length of the carbon chains present in typical fatty acid chains in triglycerides, the cetane rating of a diesel based on a biocomponent feed is typically greater than 60 for a primarily paraffinic diesel fuel sample. Although preserving olefins reduces the cetane, the cetane number for olefinic diesel boiling range molecules from a biocomponent feed is still greater than about 60. A typical diesel fuel specification requires a cetane rating of between 40 and 50. Thus, a diesel fuel or diesel fuel additive derived from a biocomponent feed is beneficial for the cetane rating when blended with a typical mineral diesel fuel. However, even though diesel fuels from biocomponent sources are suitable based on cetane rating, the amount of such fuels that can be blended with a mineral feed is conventionally limited due to poor cold flow properties. By preserving an increased number of the naturally occurring olefins in a diesel fuel derived from a biocomponent source, an increased amount of the biocomponent diesel fuel can be blended with a mineral diesel fuel while still preserving desired cold flow properties.

As an example, n-octadecane ($C_{18}H_{38}$) has a melting point of 30° C., a cetane number of 102.6, and a kinematic viscosity at 100° F. (38° C.) of 4.13 centistokes. Although the cetane number of n-octadecane is high, this molecule is a solid at room temperature. This limits the amount of n-octadecane that can be present in a diesel fuel. A corresponding molecule with one olefin, octadecene ($C_{18}H_{36}$) also has a relatively high cetane number of 90. However, the melting point for octadecene is 18° C. and the kinematic viscosity at 100° F. (38° C.) is 3.53 centistokes. Due to the more favorable properties of octadecene, a larger amount of octadecene can be added to a diesel fuel or diesel fuel additive while maintaining cold flow properties for the overall combined diesel fuel that will satisfy a cold flow specification.

In addition to providing improved cold flow properties, preserving olefins can reduce the amount of hydrogen consumption required to deoxygenate a feed from a biocomponent source. Under conventional hydrotreating conditions, substantially all olefins present in a diesel boiling range feed will be saturated during a deoxygenation process. For a triglyceride feed with an average of 1.5 olefins per fatty acid chain, the hydrogen required for saturation of olefins can correspond to roughly 200 scf/B (33.7 $Nm^3/m^3$) to 300 scf/B (50.5 $Nm^3/m^3$) of hydrogen in addition to the hydrogen required for deoxygenation. In another example, some proposed diesel feeds from biologically derived sources include substantial amounts of eicosapentaenoic acids, which are fatty acids with 20 total carbons and 5 olefin bonds. A feed of eicosapentaenoic acid would require over 2000 scf/B (337 $Nm^3/m^3$) of hydrogen just for saturation of olefins. Any olefins that are preserved during deoxygenation of such feeds will result in a corresponding decrease in the amount of hydrogen consumed during deoxygenation. For example, reaction conditions that preserve 50% of the olefins present in a triglyceride containing feed will result in a corresponding roughly 50% decrease in the amount of hydrogen consumed for olefin saturation. The hydrogen consumed by the actual deoxygenation reactions is not directly impacted by the preservation of olefins in a feed. In addition to reducing hydrogen consumption, olefin preservation also reduces the exotherm generated due to olefin saturation.

Further Hydroprocessing of Product Fractions

After separation of propylene from the final stage of a reaction system, it may be desirable to further hydroprocess the liquid effluent. An example of further processing can be to catalytically dewax the liquid effluent to improve the cold flow properties of the effluent. Because some types of dewaxing catalysts are sensitive to the presence of oxygen, it may also be desirable to hydrotreat the liquid effluent prior to dewaxing. This will typically reduce the olefin content of the liquid effluent, but the subsequent dewaxing can offset or even result in a net improvement of the cold flow properties of a diesel product formed from the liquid effluent.

A suitable catalyst for hydrotreatment can comprise, consist essentially of, or be a catalyst composed of one or more Group VIII and/or Group VIB metals on a support such as a metal oxide support. Suitable metal oxide supports can include relatively low acidic oxides such as silica, alumina, silica-aluminas, titania, zirconia, or a combination thereof. The supported Group VIII and/or Group VIB metal(s) can include, but are not limited to, Co, Ni, Fe, Mo, W, Pt, Pd, Rh, Ir, and combinations thereof. Individual hydrogenation metal embodiments can include, but are not limited to, Pt only, Pd only, or Ni only, while mixed hydrogenation metal embodiments can include, but are not limited to, Pt and Pd, Pt and Rh, Ni and W, Ni and Mo, Ni and Mo and W. Co and Mo, Co and Ni and Mo, Co and Ni and W, or another combination. When only one hydrogenation metal is present, the amount of that hydrogenation metal can be at least about 0.1 wt % based on the total weight of the catalyst, for example at least about 0.5 wt % or at least about 0.6 wt %. Additionally or alternately when only one hydrogenation metal is present, the amount of that hydrogenation metal can be about 5.0 wt % or less based on the total weight of the catalyst, for example about 3.5 wt % or less, about 2.5 wt % or less, about 1.5 wt % or less, about 1.0 wt % or less, about 0.9 wt % or less, about 0.75 wt % or less, or about 0.6 wt % or less. Further additionally or alternately when more than one hydrogenation metal is present, the collective amount of hydrogenation metals can be at least about 0.1 wt % based on the total weight of the catalyst, for example at least about 0.25 wt %, at least about 0.5 wt %, at least about 0.6 wt %, at least about 0.75 wt %, or at least about 1 wt %. Still further additionally or alternately when more than one hydrogenation metal is present, the collective amount of hydrogenation metals can be about 35 wt % or less based on the total weight of the catalyst, for example about 30 wt % or less, about 25 wt % or less, about 20 wt % or less, about 15 wt % or less, about 10 wt % or less, or about 5 wt % or less. In embodiments wherein the supported metal comprises a noble metal, the amount of noble metal(s) is typically less than about 2 wt %, for example less than about 1 wt %, about 0.9 wt % or less, about 0.75 wt % or less, or about 0.6 wt % or less. The amounts of metal(s) may be measured by methods specified by ASTM for individual metals, including but not limited to atomic absorption spectroscopy (AAS), inductively coupled plasma-atomic emission spectrometry (ICP-AAS), or the like.

Hydrotreating conditions can typically include temperatures of about 500° F. (260° C.) to about 750° F. (399° C.), hydrogen partial pressures of from about 250 psig to about 5000 psig (1.8 MPa to 34.6 MPag), liquid hourly space velocities of from 0.05 $h^{-1}$ to 10 $h^{-1}$, and hydrogen treat gas rates of from 35.6 $sm^3/m^3$ to 1781 $sm^3m^3$ (200 SCF/B to 10,000 SCF/B). In other embodiments, the conditions can include temperatures in the range of about 600° F. (343° C.) to about 700° F. (371° C.), hydrogen partial pressures of from about 500 psig to about 3000 psig (3.5 MPag-20.9 MPag), liquid hourly space velocities of from about 0.2 $h^{-1}$ to about 2 $h^{-1}$ and hydrogen treat gas rates of from about 213 $sm^3/m^3$ to about 1068 $sm^3/m^3$ (1200 SCF/B to 6000 SCF/B). The different ranges of temperatures can be used based on the type of feed and the desired hydrotreatment result.

Suitable dewaxing catalysts can include molecular sieves such as crystalline aluminosilicates (zeolites). In an embodiment, the molecular sieve can comprise, consist essentially of, or be ZSM-5, ZSM-22, ZSM-23, ZSM-35, ZSM-48, zeolite Beta, or a combination thereof, for example ZSM-23 and/or ZSM-48, or ZSM-48 and/or zeolite Beta. Optionally but preferably, molecular sieves that are selective for dewaxing by isomerization as opposed to cracking can be used, such as ZSM-48, zeolite Beta, ZSM-23, or a combination thereof. Additionally or alternately, the molecular sieve can comprise, consist essentially of, or be a 10-member ring 1-D molecular sieve. Optionally but preferably, the dewaxing catalyst can include a binder for the molecular sieve, such as alumina, titania, silica, silica-alumina, zirconia, or a combination thereof, for example alumina and/or titania or silica and/or zirconia and/or titania.

One characteristic that can impact the activity of the molecular sieve is the ratio of silica to alumina ($Si/Al_2$ ratio) in the molecular sieve. In an embodiment, the molecular sieve can have a silica to alumina ratio of about 200:1 or less, for example about 150:1 or less, about 120:1 or less, about 100:1 or less, about 90:1 or less, or about 75:1 or less. Additionally or alternately, the molecular sieve can have a silica to alumina ratio of at least about 30:1, for example at least about 40:1, at least about 50:1, or at least about 65:1.

Aside from the molecular sieve(s) and optional binder, the dewaxing catalyst can also optionally but preferably include at least one metal hydrogenation component, such as a Group VIII metal. Suitable Group VIII metals can include, but are not limited to, Pt, Pd, Ni, or a combination thereof. When a metal hydrogenation component is present, the dewaxing catalyst can include at least about 0.1 wt % of the Group VIII metal, for example at least about 0.3 wt %, at least about 0.5 wt %, at least about 1.0 wt %, at least about 2.5 wt %, or at least about 5.0 wt %. Additionally or alternately, the dewaxing catalyst can include about 10 wt % or less of the Group VIII metal, for example about 5.0 wt % or less, about 2.5 wt % or less, about 1.5 wt % or less, or about 1.0 wt % or less.

In some embodiments, the dewaxing catalyst can include an additional Group VIB metal hydrogenation component, such as W and/or Mo. In such embodiments, when a Group VIB metal is present, the dewaxing catalyst can include at least about 0.5 wt % of the Group VIB metal, for example at least about 1.0 wt %, at least about 2.5 wt %, or at least about 5.0 wt %. Additionally or alternately in such embodiments, the dewaxing catalyst can include about 20 wt % or less of the Group VIB metal, for example about 15 wt % or less, about 10 wt % or less, about 5.0 wt % or less, about 2.5 wt % or less, or about 1.0 wt % or less. In one preferred embodiment, the dewaxing catalyst can include Pt and/or Pd as the hydrogenation metal component. In another preferred embodiment, the dewaxing catalyst can include as the hydrogenation metal components Ni and W, Ni and Mo, or Ni and a combination of W and Mo.

In various embodiments, the dewaxing catalyst used according to the invention can advantageously be tolerant of the presence of sulfur and/or nitrogen during processing. Suitable catalysts can include those based on zeolites ZSM-48 and/or ZSM-23 and/or zeolite Beta. It is also noted that ZSM-23 with a silica to alumina ratio between about 20:1 and about 40:1 is sometimes referred to as SSZ-32. Additional or alternate suitable catalyst bases can include 1-dimensional 10-member ring zeolites. Further additional or alternate suitable catalysts can include EU-2, EU-11, and/or ZBM-30.

A bound dewaxing catalyst can also be characterized by comparing the micropore (or zeolite) surface area of the catalyst with the total surface area of the catalyst. These surface areas can be calculated based on analysis of nitrogen porosimetry data using the BET method for surface area measurement. Previous work has shown that the amount of zeolite content versus binder content in catalyst can be determined from BET measurements (see, e.g., Johnson, M. F. L., *Jour. Catal.*, (1978) 52, 425). The micropore surface area of a catalyst refers to the amount of catalyst surface area provided due to the molecular sieve and/or the pores in the catalyst in the BET measurements. The total surface area represents the micropore surface plus the external surface area of the bound catalyst. In one embodiment, the percentage of micropore surface area relative to the total surface area of a bound catalyst can be at least about 35%, for example at least about 38%, at least about 40%, or at least about 45%. Additionally or alternately, the percentage of micropore surface area relative to total surface area can be about 65% or less, for example about 60% or less, about 55% or less, or about 50% or less.

Catalytic dewaxing can be performed by exposing a feedstock to a dewaxing catalyst under effective (catalytic) dewaxing conditions. Effective dewaxing conditions can include can be carried out at temperatures of about 550° F. (288° C.) to about 840° F. (449° C.), hydrogen partial pressures of from about 250 psig to about 5000 psig (1.8 MPag to 34.6 MPag), and hydrogen treat gas rates of from 35.6 sm$^3$/m$^3$ to 1781 sm$^3$/m$^3$ (200 SCF/B to 10,000 SCF/B). In other embodiments, the conditions can include temperatures in the range of about 600° F. (343° C.) to about 815° F. (435° C.), hydrogen partial pressures of from about 500 psig to about 3000 psig (3.5 MPag-20.9 MPag), and hydrogen treat gas rates of from about 213 sm$^3$/m$^3$ to about 1068 sm$^3$/m$^3$ (1200 SCF/B to SCF/B). The liquid hourly space velocity (LHSV) of the feed relative to the dewaxing catalyst can be characterized can be from about 0.1 hr$^{-1}$ to about 10 hr$^{-1}$.

Separation of Propylene from Gas Phase Components

After performing a (partial) deoxygenation under effective conditions, propylene can be present as one of a variety of gas phase components. These gas phase components can also include, but are not limited to, other deoxygenation reaction products such as $H_2O$, $CO_2$, and/or CO; gases present in the reaction environment, such as $H_2$, $H_2S$, $N_2$, and/or other inert gases; potential light ends cracking products from the deoxygenation reaction; and propane, which is the expected typical product generated from the glycerol backbone of a triglyceride during a deoxygenation reaction.

In order to recover propylene, the gas phase products can first be separated from the liquid products from the deoxygenation reaction, which will typically be diesel boiling range and/or naphtha boiling range molecules. The propylene can then be separated from the remaining gas phase components. Due to the similarity in boiling point between propane and propylene, simple distillation techniques may not be effective. One option for distillation is to use a distillation method with a sufficiently large number of tray equivalents, so that the separation of propane from propylene can be performed in spite of the similarity in boiling point. Any convenient method for providing a distillation column with a sufficient number of equivalent trays can be used. For example, cryogenic distillation columns may be beneficial for propane-propylene separations. Depending on the embodiment, at least about 0.25 wt % of propylene can be recovered relative to the weight of the input feed, such as at least about 0.5 wt %, or at least about 1.0 wt %.

Alternatively, the amount of propylene recovery can be expressed relative to the weight of triglycerides in the input feed. Propylene formed according to the invention will primarily form based on separation of the glycerol backbone in triglycerides from the side chains. This is in contrast to propylene formed by more severe processing methods, such as propylene formed by cracking of a feed. Depending on the embodiment, at least about 0.5 wt % of propylene can be recovered relative to the weight of triglycerides in the input feed, such as at least about 1.0 wt %, or at least about 2.0 wt %.

Still another option for characterizing the amount of propylene recovered is based on the relative weight fraction of propylene recovered versus propane recovered. The relative weight fraction is defined as a ratio of the weight of recovered propylene versus the weight of recovered propane. The relative weight fraction is an indication of the selectivity of a deoxygenation method for generating propylene in favor of propane during deoxygenation. Depending on the aspect, the relative weight fraction of propylene versus propane can be at least about 0.25, such as at least about 0.3, or at least about 0.4. For typical deoxygenation conditions, it is expected that the relative weight fraction of propylene versus propane will be about 5.0 or less, such as about 1.5 or less or about 1.0 or less.

Another option for separating propylene from a gas phase mixture is to use a gas separation train similar to the separation trains used in some fluid catalytic cracking (FCC) reaction systems. Propylene is also an output product from FCC reactions. One option is to introduce the gas phase output from deoxygenation to the gas processing train of an existing FCC reaction system to perform propylene recovery. The gas phase output from deoxygenation can optionally be processed prior to feeding the gas phase output into the FCC gas processing train. For example, the gas phase output can be passed through an amine scrubber to remove contaminant species such as $H_2S$ or $CO_2$. Another option is to use a pressure swing adsorber system to remove $CO_2$ and/or CO.

The gas phase output from the deoxygenation reaction can be separated from the liquid phase output at any convenient time. One option is to perform a gas-liquid separation after the feed has passed through all stages of the deoxygenation reaction. Another option is to perform an intermediate separation. For example, the catalyst(s) for performing deoxygenation may be provided in a plurality of catalyst beds. At least a portion of the gas phase output can be withdrawn from the deoxygenation reaction system between such catalyst beds. Withdrawing at least a portion of the gas phase output at an intermediate stage will reduce the amount of catalyst that at least some of the propylene is exposed to. This reduces the amount of propylene lost to subsequent olefin saturation in later portions of the deoxygenation catalyst bed(s).

Examples of Processing Configurations

FIG. 1 schematically shows an example of a processing configuration suitable for deoxygenating a biocomponent feed. The configuration in FIG. 1 also provides for separation of a propylene output from the deoxygenation products. In FIG. 1, a source of biocomponent feed 102 provides a feedstock for processing. Any convenient source 102 can be used, such as tankage for storing a biocomponent feed until it is ready for use. Preferably, the biocomponent feed is a feed that contains triglycerides. Optionally, the output 103 from biocomponent feed source 102 is passed through a feed surge drum 104 to improve the consistency of the flow rate from the feed source. The output 105 from optional feed surge drum 104 is then passed into a reactor 110. The output 105 can be heated (not shown) prior to entering reactor 110. A hydrogen-containing flow 109 is also introduced into reactor 110. Although the hydrogen-containing flow 109 is shown in FIG. 1 as co-current with the feed, the hydrogen-containing flow 109 may alternatively or additionally be introduced into reactor 110 counter-current to the feed. A portion 152 of the hydrogen-containing flow 109 can be from a fresh hydrogen source, or the portion 152 of the hydrogen-containing flow 109 can be at least partially based on an exit hydrogen flow from another reaction, such as the hydrogen output from a hydroprocessing reaction. The portion 152 can be combined with a recycled hydrogen-containing stream 159 generated from an output stream of reactor 110 to form hydrogen-containing flow 109. In FIG. 1, reactor 110 is shown as having two stages 113 and 117 for deoxygenation. Each stage corresponds to a bed of catalyst. Alternatively, reactor 110 can include any convenient number of beds of catalyst, such as one bed or a plurality of beds, or reactor 110 can even correspond to multiple reactors.

In FIG. 1, two output streams are generated from reactor 110. A primary output stream 115 exits from the reactor after passing through both stages 113 and 117. The output stream 115 includes both a gas phase and a liquid phase effluent that is passed into gas-liquid separator(s) 122 for separation. Optionally, a second gas phase output stream 119 can also be withdrawn from reactor 110 at a location between stages or beds 113 and 117. Withdrawing a gas phase output stream 119 prior to the second stage is beneficial for preserving propylene. By withdrawing the gas phase output stream between the beds, any propylene formed during the deoxygenation reaction in bed or stage 113 is not exposed to the additional catalyst in stage 117, thus reducing the likelihood that propylene formed in stage 113 will be converted to propane.

Separator (or separators) 122 separate the outputs from reactor 110 into a gas phase output 123 and a liquid phase output 145. Liquid phase output 145 is suitable for further processing as, for example, a diesel boiling range product. Gas phase output 123 will typically include a variety of species, such as one or more of $H_2S$, $H_2O$, $CO_2$, $NH_3$, CO, and hydrocarbons with short carbon chain lengths, such as $C_1$-$C_4$ hydrocarbons. The gas phase output 123 can be purified to isolate a desirable product, such as propylene, from other impurities generated during deoxygenation, such as $H_2S$ or $CO_2$. In an initial purification step, a cold separation device 124 is shown for removing water from the gas phase output. This generates a water output stream 129 and a stream 125 containing the remaining gas phase species. An amine scrubber 130 or other separation device for removing $H_2S$ and $CO_2$ can then be used to purify stream 125. For the amine scrubber shown in FIG. 1, a counter-current flow of an amine such monoethanol amine can be introduced 133 into scrubber 130 for removal of $H_2S$ and/or $CO_2$. The monoethanol amine enriched in the gas phase impurities is withdrawn 139 from the scrubber for recycling of the amine. The output stream 135 can then be further separated 150 to separate a hydrogen stream 159 from the remaining stream 155 that contains propylene and potentially other light ends. The remaining stream 155 that includes at least propylene can be passed into a system for performing separations on compounds with similar boiling points, such as a cryogenic separator or an existing FCC separation system.

Figure 2:
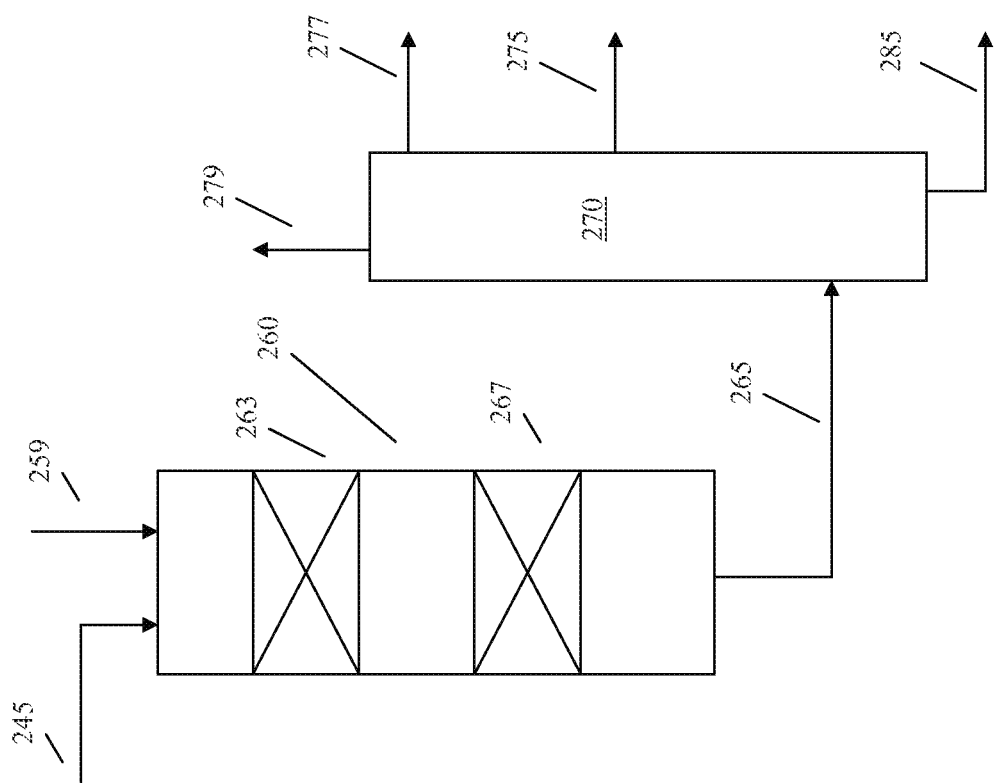
FIG. 2 schematically shows a reaction system suitable for performing a process according to an embodiment of the invention.

FIG. 2 schematically shows an example of a reaction system suitable for processing a diesel boiling range input stream that includes olefinic diesel. In FIG. 2, input stream 245 corresponds to a diesel boiling range stream where at least a portion of the diesel boiling range molecules are olefins, such as a stream generated by deoxygenation of a biocomponent feed under effective conditions as described herein. The various types of processing shown in FIG. 2 represent optional processes that can be performed on a diesel boiling range stream. While these optional processes are not necessary, the optional processes can improve the diesel boiling range stream by removing any remaining oxygen and/or improving cold flow properties.

The input stream 245 can be passed into a reactor 260 for hydrotreatment, catalytic dewaxing, or a combination thereof. FIG. 2 shows an example where the input stream 245 is hydrotreated and then catalytically dewaxed in reactor 260. Reactor 260 is shown as including a stage 263 for hydrotreatment of a feed and a downstream stage 267 for catalytic dewaxing. The hydrotreatment stage 263 is used to perform hydrotreatment under mild conditions to complete the removal of any oxygen remaining in stream 255. Preferably, the hydrotreatment conditions are effective for removal of any remaining oxygen while reducing or minimizing the amount of olefin saturation. The mild hydrotreatment allows catalytic dewaxing to be performed 267 using a catalyst that is otherwise sensitive to oxygen content. The catalytic dewaxing improves the cold flow properties of the diesel boiling range molecules present in stream 255. In the example shown in FIG. 2, the hydrogen input 259 for the hydrotreatment and dewaxing reactions is passed into reactor 260 in a co-current manner. In an alternative configuration, hydrogen input 259 can be passed into reactor 260 in a counter-current manner. The effluent 265 from reactor 260 is then passed into a fractionator for separation of the effluent into desired fractions. Examples of fractions generated from an olefinic diesel boiling range feed can include a gas phase or light ends fraction 279, one or more naphtha and/or kerosene fractions 277, and one or more diesel fractions 275, and one or more lubricant base stock or heavier fractions 285. The light ends fraction 279 represent molecules created due to cracking of input stream 245 during exposure to either the optional acidic catalyst in reactor 250 or exposure to the optional hydrotreatment and/or dewaxing catalysts in reactor 260. The naphtha or kerosene products 277 can result from cracking in the presence of a deoxygenation catalyst, the acidic catalyst for oligomerization, the hydrotreating catalysts, or the dewaxing catalysts. The diesel boiling range fractions 275 are the expected output from deoxygenation of a biocomponent feed. For example, deoxygenation of a triglyceride-containing feed will typically result in formation of approximately diesel boiling range molecules from the fatty acid chains in the triglycerides. Some of these fatty acid chains may result in olefins or paraffins that boil in the lubricant range, corresponding to fractions 285.

Example of Deoxygenating Biocomponent Feed with a Metal Sulfide Catalyst

A triglyceride-containing feedstock was treated under effective deoxygenation conditions in the presence of hydrogen, CO, and a commercial hydrotreating catalyst under a variety of conditions. In various runs, the feedstock was exposed to either a commercially available CoMo hydrotreating catalyst or a commercially available NiMo hydrotreating catalyst. The feedstock was 60 wt % of a soybean oil combined with 40 wt % of a desulfurized diesel boiling range product stream. Although a mineral feed was mixed with the soybean oil, the mineral feed was selected to roughly mimic a configuration where 40 wt % of the feed is a recycled effluent from treating the bio-origin feed (in this case soybean oil). The feed was spiked with ~100 wppm S, in order to maintain the sulfided state of the hydrotreating catalysts. Although an organic sulfur-containing spiking agent was used, it is believed that a similar effect can be achieved by introduction of $H_2S$ into the reaction environment.

In the deoxygenation runs, the feed was exposed to the hydrotreating catalyst under the conditions shown in Table 1. For the NiMo catalyst examples and for the CoMo catalyst at the temperature of 575° F. (302° C.), the conditions shown in Table 1 were sufficient to substantially deoxygenate the feed. However, due to the presence of 2000 wppm CO, the conditions shown in Table 1 for exposing the feed to a CoMo catalyst at 500° F. (260° C.) were not sufficient to fully deoxygenate the feed. The incomplete deoxygenation when exposing the feed to a CoMo catalyst at 500° F. (260° C.) can be seen, for example, in the combined levels of propylene yield on bio and propane yield on bio shown in Table 1. The "yield on bio" rows indicate the amount of propylene and propane, respectively, generated relative to the amount of bio-origin feedstock in the feed, as opposed to the amounts of propylene and propane generated relative to the total input feed to the reactor. For the soybean oil used in these runs, it is believed that full deoxygenation of the soybean oil would correspond to combined amounts for propylene yield on bio and propane yield on bio of between about 4.8 wt % and about 5.1 wt %. This is based on the expected yields of propane and propylene if a reaction was 100% selective toward formation of either propane or propylene. For example, a 100% selectivity for propane formation would result in a propane yield of 5.1 wt % on bio, while a 100% selectivity for propylene formation would result in a propylene yield of 4.8 wt % on bio.

As shown in Table 1, processing over the commercially available NiMo catalyst at either temperature or processing over the commercially available CoMo catalyst at 575° F. (302° C.) resulted in a combined propylene yield on bio and propane yield on bio of about 4.9 wt % or about 5.0 wt %, indicating substantially complete removal of oxygen from the feed. However, processing over the commercially available CoMo hydrotreating catalyst at 500° F. (260°) resulted in about 3.3 wt % of combined propylene and propane yield. Thus, the runs shown in Table 1 would be suitable for use in a reaction system where multiple deoxygenation stages or beds are present, with the results shown below corresponding to propylene that can be recovered from an effluent between stages or beds.

TABLE 1

Propylene Generation during Hydrodeoxygenation

| | CoMo | | NiMo | |
|---|---|---|---|---|
| Temp, ° F. | 500 | 575 | 540 | 575 |
| Pressure, psig | 400 | 400 | 400 | 400 |
| LSHV, hr[1] | 1 | 1 | 1 | 1 |
| CO in treat gas, ppm | 2000 | 2000 | 2000 | 2000 |
| Treat gas rate, scf/bbl | 3500 | 3500 | 3500 | 3500 |
| Bio content, wt % | 60 | 60 | 60 | 60 |
| Propylene yield on bio, wt % | 1.1 | 0.2 | 0.1 | 0.8 |

TABLE 1-continued

Propylene Generation during Hydrodeoxygenation

|  | CoMo |  | NiMo |  |
|---|---|---|---|---|
| Propane yield on bio, wt % | 2.2 | 4.8 | 4.9 | 4.1 |
| Propylene/Propane, wt frac. | 0.49 | 0.05 | 0.02 | 0.20 |

As shown in Table 1, hydrodeoxygenating a triglyceride-containing feed (soybean oil) in the presence of a CoMo catalyst and in the presence of CO resulted in production of propylene, as opposed to production of only propane. For the CoMo catalyst, the amount of propylene decreased as the temperature increased. Conversely, the amount of propylene increased with temperature for the NiMo catalyst runs. It is noted that for the NiMo deoxygenation runs, the oxygen conversion was the same to within experimental error at the temperatures of 540° F. and 575° F.

It is noted that the above runs were performed at 400 psig (2.8 MPag) of total pressure. Similar runs at 800 psig with the commercially available CoMo catalyst and the commercially available NiMo catalyst had no observable propylene yield.

ADDITIONAL EMBODIMENTS

Embodiment 1

A method for processing a biocomponent feedstock, comprising: exposing a feedstock, the feedstock comprising at least 40 wt % of a biocomponent feed containing triglycerides, to a first catalyst in the presence of hydrogen and at least 300 vppm of CO under first effective deoxygenation conditions for forming an at least partially deoxygenated effluent, the first catalyst comprising a Group VI metal and a Group VIII non-noble metal, the at least partially deoxygenated effluent having an oxygen content that is at least 40% less than an oxygen content of the feedstock; separating the at least partially deoxygenated effluent to form a gas phase effluent comprising propylene and a liquid phase effluent; and separating at least a portion of the propylene from the gas phase effluent.

Embodiment 2

The method of Embodiment 1, wherein the propylene separated from the gas phase effluent comprises at least about 0.25 wt % of propylene relative to the weight of the biocomponent feed, such as at least 0.5 wt % or at least about 1.0 wt %, or wherein the relative weight fraction of propylene to propane is at least about 0.25, such as at least about 0.3, or at least about 0.4, or a combination thereof.

Embodiment 3

The method of any of the above embodiments, wherein the biocomponent feed comprises at least 40 wt % of triglycerides, such as at least about 50 wt %.

Embodiment 4

The method of any of the above embodiments, wherein the liquid phase effluent comprises at least about 10 wt % olefins, the liquid phase effluent has an olefin to paraffin ratio of at least about 0.03, such as at least about 0.04 or at least about 0.05, or a combination thereof.

Embodiment 5

The method of any of the above embodiments, wherein the at least one Group VI metal is tungsten or molybdenum, preferably molybdenum, and the at least one Group VIII non-noble metal is nickel or cobalt, preferably cobalt, and more preferably the first catalyst comprises cobalt and molybdenum.

Embodiment 6

The method of any of the above embodiments, wherein the feedstock is exposed to the first catalyst in the presence of at least about 500 vppm of carbon monoxide, such as at least about 1000 vppm, or at least about 1500 vppm, and/or about 7000 vppm or less, such as about 4000 vppm or less.

Embodiment 7

The method of any of the above embodiments, further comprising recycling at least a portion of the gas phase effluent as a hydrogen-containing and CO-containing input for said exposing of the feedstock, wherein optionally at least a portion of $CO_2$, $H_2O$, $H_2S$, or a combination thereof is removed from the at least a portion of the gas phase effluent prior to recycling as a hydrogen-containing and CO-containing input for said exposing of the feedstock.

Embodiment 8

The method of any of the above embodiments, further comprising exposing the liquid effluent to a second catalyst in the presence of hydrogen and at least 300 vppm of carbon monoxide under second effective deoxygenation conditions for forming an effluent having an oxygen content of 300 wppm or less, the second catalyst comprising a Group VI metal and a Group VIII non-noble metal, wherein optionally the first catalyst is different from the second catalyst, the first effective deoxygenation conditions are different from the second deoxygenation conditions, or a combination thereof.

Embodiment 9

The method of Embodiment 8, further comprising separating the effluent having an oxygen content of 300 wppm or less to form at least a second gas phase effluent comprising propylene, wherein separating at least a portion of the propylene from the gas phase effluent further comprises separating at least a portion of the propylene from the second gas phase effluent.

Embodiment 10

The method of any of the above embodiments, wherein the first effective deoxygenation conditions include a temperature from about 250° C. to about 350° C., an LHSV from about 0.2 $hr^{-1}$ to about 10 $hr^{-1}$, and a hydrogen partial pressure of about 200 psig (1.4 MPag) to about 600 psig (4.1 MPag).

Embodiment 11

The method of any of the above embodiments, further comprising fractionating the liquid phase effluent to form at least a diesel product fraction.

Embodiment 12

The method of any of the above embodiments, further comprising hydrotreating the liquid phase effluent under effective hydrotreating conditions to form a hydrotreated product effluent, exposing at least one of the liquid phase effluent or the diesel product to a dewaxing catalyst under effective dewaxing conditions, or a combination thereof.

Embodiment 13

The method of Embodiment 12, wherein the hydrotreated product effluent is dewaxed prior to fractionation of the hydrotreated product effluent.

Embodiment 14

The method of any of the above embodiments, wherein the feedstock comprises from about 15 wt % to about 40 wt % triglycerides, and the effective deoxygenation conditions include a temperature from about 500° F. (293° C.) to about 600° F. (316° C.), an LHSV from about 0.2 hr$^{-1}$ to about 10 hr$^{-1}$, and a hydrogen partial pressure of about 300 psig (2.1 MPag) to about 500 psig (3.4 MPag).

Embodiment 15

The method of any of the above embodiments, wherein the at least partially deoxygenated effluent has an oxygen content of about 0.5 wt % or less.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for processing a biocomponent feedstock, comprising:
exposing a feedstock, the feedstock comprising at least 40 wt % of a biocomponent feed containing triglycerides, to a first catalyst in the presence of hydrogen and at least 300 vppm of CO under first effective deoxygenation conditions for forming an at least partially deoxygenated effluent, the first catalyst comprising a Group VI metal and a Group VIII non-noble metal, the at least partially deoxygenated effluent having an oxygen content that is at least 40% less than an oxygen content of the feedstock;
separating the at least partially deoxygenated effluent to form a gas phase effluent comprising propylene and a liquid phase effluent; and
separating at least a portion of the propylene from the gas phase effluent.

2. The method of claim 1, wherein the propylene separated from the gas phase effluent comprises at least about 0.25 wt % of propylene relative to the weight of the biocomponent feed.

3. The method of claim 1, wherein a relative weight ratio of propylene to propane in the gas phase effluent is at least about 0.25.

4. The method of claim 1, wherein the biocomponent feed comprises at least 40 wt % of triglycerides.

5. The method of claim 1, wherein the liquid phase effluent comprises at least about 10 wt % olefins.

6. The method of claim 1, wherein the liquid phase effluent has an olefin to paraffin ratio of at least about 0.03.

7. The method of claim 1, wherein the at least one Group VI metal is tungsten or molybdenum and the at least one Group VIII non-noble metal is nickel or cobalt.

8. The method of claim 7, wherein the first catalyst comprises cobalt and molybdenum.

9. The method of claim 1, wherein the feedstock is exposed to the first catalyst in the presence of at least about 500 vppm of carbon monoxide, about 5000 vppm or less of carbon monoxide, or a combination thereof.

10. The method of claim 1, further comprising recycling at least a portion of the gas phase effluent as a hydrogen-containing and CO-containing input for said exposing of the feedstock.

11. The method of claim 10, wherein at least a portion of $CO_2$, $H_2O$, $H_2S$, or a combination thereof is removed from the at least a portion of the gas phase effluent prior to recycling as a hydrogen-containing and CO-containing input for said exposing of the feedstock.

12. The method of claim 1, further comprising exposing the liquid effluent to a second catalyst in the presence of hydrogen and at least 300 vppm of carbon monoxide under second effective deoxygenation conditions for forming an effluent having an oxygen content of 300 wppm or less, the second catalyst comprising a Group VI metal and a Group VIII non-noble metal.

13. The method of claim 12, wherein the first catalyst is different from the second catalyst, the first effective deoxygenation conditions are different from the second deoxygenation conditions, or a combination thereof.

14. The method of claim 12, further comprising separating the effluent having an oxygen content of 300 wppm or less to form at least a second gas phase effluent comprising propylene, wherein separating at least a portion of the propylene from the gas phase effluent further comprises separating at least a portion of the propylene from the second gas phase effluent.

15. The method of claim 1, wherein the first effective deoxygenation conditions include a temperature from about 250° C. to about 350° C., an LHSV from about 0.2 hr$^{-1}$ to about 10 hr$^{-1}$, and a hydrogen partial pressure of about 200 psig (1.4 MPag) to about 600 psig (4.1 MPag).

16. The method of claim 1, further comprising fractionating the liquid phase effluent to form at least a diesel product fraction, and exposing at least one of the liquid phase effluent or the diesel product to a dewaxing catalyst under effective dewaxing conditions.

17. The method of claim 1, further comprising at least one of:
hydrotreating the liquid phase effluent under effective hydrotreating conditions.

18. The method of claim 1, further comprising:
hydrotreating the product effluent under effective hydrotreating conditions; and
exposing the hydrotreated product effluent to a dewaxing catalyst under effective dewaxing conditions,
wherein the hydrotreated product effluent is dewaxed prior to the fractionation of the hydrotreated product effluent.

19. The method of claim 1, wherein the feedstock comprises from about 15 wt % to about 40 wt % triglycerides, and the effective deoxygenation conditions include a temperature from about 500° F. (293° C.) to about 600° F. (316° C.), an LHSV from about 0.2 h$^{-1}$ to about 10 hr$^{-1}$, and a hydrogen partial pressure of about 300 psig (2.1 MPag) to about 500 psig (3.4 MPag).

20. The method of claim 1, wherein the at least partially deoxygenated effluent has an oxygen content of about 0.5 wt % or less.

* * * * *